United States Patent [19]
Vanney et al.

[11] Patent Number: 5,843,177
[45] Date of Patent: Dec. 1, 1998

[54] APPARATUS FOR ATTACHING A HANDLE TO AN ANNULOPLASTY RING IMPLANTATION DEVICE

[75] Inventors: Guy P. Vanney, Blaine; Kimberly A. Anderson, Eagan, both of Minn.

[73] Assignee: St. Jude Medical, Inc., St. Paul, Minn.

[21] Appl. No.: 641,914

[22] Filed: May 2, 1996

[51] Int. Cl.$^6$ ..................................................... A61F 2/24
[52] U.S. Cl. .............................. 623/2; 606/108; 606/148
[58] Field of Search ........................ 623/2, 900; 128/774; 33/511, 512; 606/108, 148, 150

[56] References Cited

U.S. PATENT DOCUMENTS

| | | | |
|---|---|---|---|
| 3,828,787 | 8/1974 | Anderson | 128/303 |
| 4,585,453 | 4/1986 | Martin et al. | 623/2 |
| 4,865,600 | 9/1989 | Carpentier et al. | 623/2 |
| 4,987,904 | 1/1991 | Wilson | 128/774 |
| 5,011,481 | 4/1991 | Myers et al. | 606/1 |
| 5,197,979 | 3/1993 | Quintero et al. | 623/2 |
| 5,290,300 | 3/1994 | Cosgrove et al. | 606/148 |
| 5,326,371 | 7/1994 | Love et al. | 623/2 |
| 5,336,258 | 8/1994 | Quintero et al. | 623/2 |
| 5,360,014 | 11/1994 | Sauter et al. | 128/774 |
| 5,403,305 | 4/1995 | Sauter et al. | 606/1 |
| 5,471,756 | 12/1995 | Bolanos et al. | 33/501.45 |
| 5,489,296 | 2/1996 | Love et al. | 623/2 |
| 5,522,884 | 6/1996 | Wright | 623/2 |

OTHER PUBLICATIONS

"Prosthetic Rings and Accessories for Tricuspid and Mitral Valvuloplasty", *Carpentier–Edwards®*, Dec. 1985, pp. 1–8.
"Techiques for Implanting the SJM® Séguin Annuloplasty Ring for Mitral Valve Repair", *St. Jude Medical*, 1996, 4 pages.

*Primary Examiner*—Randy C. Shay
*Attorney, Agent, or Firm*—Hallie A. Finucane, Esq.; Westman, Champlin & Kelly, P.A.

[57] ABSTRACT

An apparatus for manipulating an annuloplasty ring implantation device during implantation includes an elongated handle having a proximal end for grasping by a surgeon and a distal end. A locking surface is provided adjacent the distal end of the elongated handle. The elongated handle carries an engaging tip which extends distally from the locking surface. A locking key extends radially from the engaging tip. The annuloplasty ring implantation device includes an engaging tip opening formed therein adapted for receiving the engaging tip. A key slot is defined in the implantation device and extends radially from the engaging tip opening. The engaging tip and locking key may be inserted into the device at the engaging tip opening and key slot. The elongated handle is locked to the device by inserting the engaging tip and rotating the handle relative to the device such that the locking key and key slot are not aligned. This causes the device to be locked between the locking key and the locking surface. The annuloplasty ring implantation device is an annuloplasty ring holder or a annuloplasty ring sizer template.

10 Claims, 5 Drawing Sheets

APPARATUS FOR ATTACHING A HANDLE TO AN ANNULOPLASTY RING IMPLANTATION DEVICE

FIELD OF THE INVENTION

The present invention relates to implantation of annuloplasty rings. More specifically, the invention relates to attachment of an elongated handle to annuloplasty ring implantation devices.

BACKGROUND OF THE INVENTION

Certain types of diseases and defects in heart valves are known to reduce the efficiency of the natural valve. One such defect occurs when the radius of the valve is enlarged or deformed such that the cusps of the natural valve do not form a seal when the valve is in a closed position, which allows regurgitation of blood through the cusps.

Such defects in the heart valve are repaired using a surgical technique known as annuloplasty in which a prosthetic annuloplasty ring is affixed in the patient proximate the defective natural heart valve. Prosthetic annuloplasty rings may be of varying shapes and varying compliances. One such annuloplasty ring is shown and described in French Patent No. 2 708 458.

During the implantation surgery, it is necessary for the surgeon to size the annulus of the natural valve such that the proper size annuloplasty ring may be selected. Typically, the surgeon uses a series of sizer templates of varying dimensions which are positioned proximate the natural valve, and observed relative to the natural valve, to determine the size of the natural valve relative to the sizer template. Once the appropriate sizer template is identified, the corresponding appropriately sized annuloplasty ring is selected by the surgeon. This annuloplasty ring is then sutured proximate the natural heart valve and provides reinforcement and shape to the annulus of the natural valve such that the cusps of the natural valve completely close, thereby preventing the regurgitation of blood.

During implantation, an annuloplasty ring holder is used which releasably holds the annuloplasty ring. Both the annuloplasty ring holder and the sizer template are manipulated at the distal end of an elongated handle by the surgeon. The coupling between the distal tip of the handle and the ring holder or sizer template should be such that the two may be easily separated. For example, the surgeon must typically try a number of different sizer templates before locating the proper sizer template. Therefore, it is desirable for the surgeon to be able to quickly remove and replace the sizer templates on the distal end of the handle. Similarly, it is desirable for the handle to be easily removed from the holder during implantation of the annuloplasty ring. At the same time, the annuloplasty sizer template or holder should be securely attached to the handle to prevent unintentional separation of the sizer template or holder from the distal end of the handle.

The prior art has used a number of techniques for coupling the distal end of the elongated handle to the sizer template or holder. One such technique is the use of a tapered distal tip on the handle which is pressed into a similarly tapered opening in the sizer template or holder which generally conforms to the tapered distal tip. This provides a friction fit between the sizer template or holder and the distal tip of the handle which may be separated by applying a separation force between the holder/sizer and handle. This technique does not provide a positive lock between the handle and the sizer template or ring holder, and the engagement forces may vary due to dimensional tolerances or wear. Therefore, it may be difficult to remove the handle from the holder or sizer when the holder or sizer is positioned adjacent the natural valve because the separating force must be applied to the holder or sizer in the chest cavity while the handle is pulled from the holder or sizer. Alternatively, if the friction fit between the two pieces is too loose, the holder will slip off of the handle. It is difficult to accurately control the size of the pieces and thus the engagement force is difficult to control between these extremes.

Another technique for coupling a handle to a holder is described in U.S. Pat. No. 5,290,300 to Cosgrove et al., entitled "FLEXIBLE SUTURE GUIDE AND HOLDER". FIGS. 3 and 4 of the Cosgrove et al. reference show attaching a handle to a holder. The handle includes notch 48 which receives a spoke 39. The handle is coupled to the holder by forcing the two together and rotating the handle such that the spoke rests on a landing 50. The technique described in the Cosgrove reference is undesirable because it presents a relatively large obstacle which makes viewing the implantation difficult. Furthermore, the handle shown in the Cosgrove reference includes a blind hole which is difficult to sterilize and clean. This device also may require special sterilization packaging.

SUMMARY OF THE INVENTION

The present invention is an apparatus for manipulating an annuloplasty ring implantation device, such as an annuloplasty ring holder or a sizer template, during implantation of an annuloplasty ring in a patient. The apparatus comprises an elongated handle having a proximal end for grasping by a surgeon and a distal end. A locking surface is provided in the elongated handle at the distal end. An engaging tip extends distally from the locking surface of the handle. A locking key extends generally radially from the engaging tip. The annuloplasty ring implantation device includes an engaging tip opening formed therein which extends from a top surface of the device generally inward, into the device, and is adapted for receiving the engaging tip. A key slot is provided which extends radially outward from the engaging tip opening. The key slot is positioned and of shape to receive the locking key. The elongated handle is selectively attached to the annuloplasty ring implantation device by placing the engaging tip into the engaging tip opening with the locking key aligned with the key slot. Once the engaging tip is placed into the engaging tip opening, the handle is rotated axially relative to the implantation device such that the locking key is not aligned with the key slot. This causes the device to be held between the locking surface and the locking key. The elongated handle is separated from the annuloplasty ring implantation device by rotating the elongated handle such that the locking key is aligned with the key slot thereby allowing the engaging tip to be removed from the engaging tip opening.

In one embodiment, a spring is carried on the engaging tip adjacent the locking surface to urge the locking surface and elongated handle away from the annuloplasty ring implantation device. In one embodiment, a notch is provided in a bottom surface of the annuloplasty implantation device to receive the locking key and thereby prevent inadvertent rotation of the elongated handle relative to the annuloplasty ring implantation device during surgery.

DETAILED DESCRIPTION OF THE PREFERRED EMBODIMENTS

Figure 1:
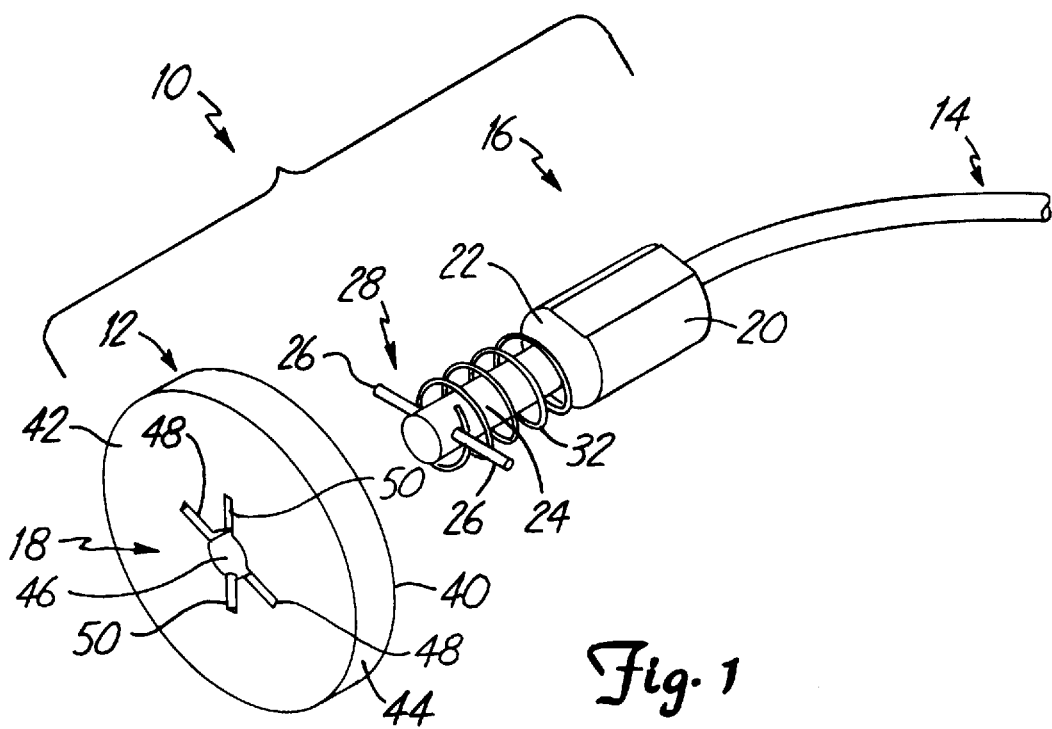
FIG. 1 is an exploded perspective view of an apparatus including an elongated handle and an annuloplasty ring implantation device.

FIG. 1 is an exploded perspective view showing an apparatus 10 for manipulating annuloplasty ring implantation device 12. As used herein, the term annuloplasty ring implantation device includes annuloplasty sizer templates and annuloplasty ring holders. Apparatus 10 includes elongated handle 14 having distal end 16 which couples to attachment area 18 of implantation device 12. Distal tip 16 includes an abutting element 20 which provides a locking surface 22. An engaging tip 24 extends distally from abutting element 20 and locking surface 22. Engaging tip 24 carries locking keys 26 which extend radially outward from the engaging tip 24 at its distal end 28. In one embodiment, locking keys 26 are formed by a pin which is secured in engaging tip 24. A spring member 32 is formed of a coiled spring, is captured on engaging tip 24 between locking surface 22 and locking keys 26 and extends co-axially with engaging tip 24. Alternatively, if pin 26, tip 24, abutting element 20, or device 12 has some elasticity or is compliant, spring member 32 may not be needed. Locking surface 22 and spring member 32 provide a force against device 12 which secures device 12 to handle 14. Further, surface 22 and spring 32 provide a disengagement force against device 12 as explained below.

Implantation device 12 includes a top surface 40, a bottom surface 42 and a side wall 44 extending therebetween. An engaging tip opening 46 extends generally through the center of device 12 between the top surface 40 and the bottom surface 42. Opening 46 may be at any desired position. The engaging tip opening 46 is of size and shape to generally conform to the engaging tip 24 of elongated handle 14. Key slots 48 also extend between the top surface 40 and the bottom surface 42 and are positioned radially on opposing sides of engaging tip opening 46. Key slots 48 extend radially outward from engaging tip opening 46 and are of size and shape to generally conform to locking keys 26 and allow passage of locking keys 26 therethrough. Key notches 50 are formed in bottom surface 42 and are depressions or recesses in surface 42. As shown in FIG. 1, key notches 50 extend radially outward from engaging tip opening 46 and are positioned approximately 90° from, and perpendicular, to key slots 48, although key notches may be formed at other positions between key slots 48.

Figure 2:
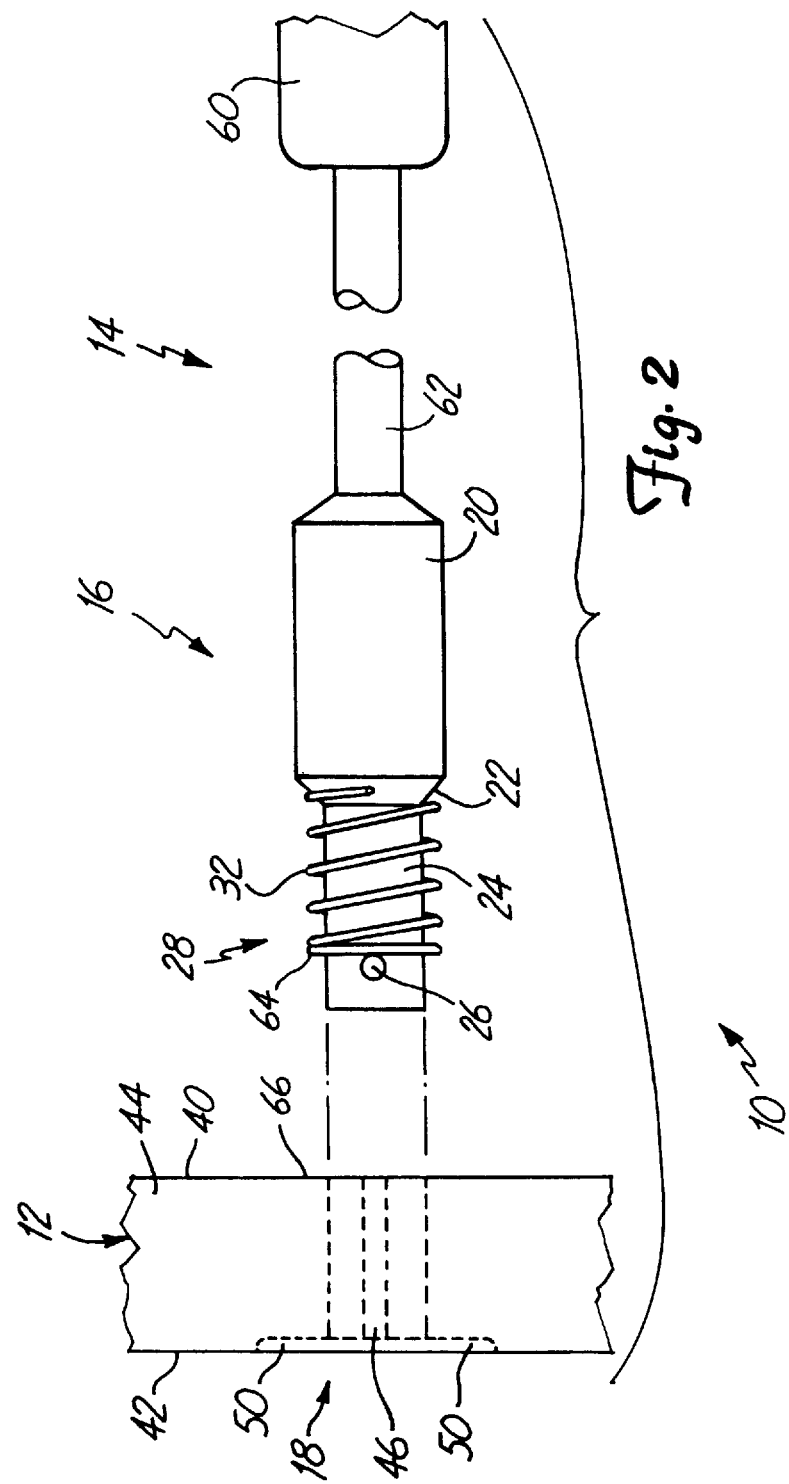
FIG. 2 is a side plan view of the elongated handle and annuloplasty ring implantation device of FIG. 1.

FIG. 2 is an exploded side plan view of apparatus 10 showing elongated handle 14 and distal end 16 positioned proximate annuloplasty ring implantation device 12. In FIG. 2, abutting element 20 and locking surface 22 are shown in a slightly different embodiment than in FIG. 1. As shown in FIGS. 1 and 2, locking surface 22 may be of varying configurations, including a pin or radial protrusion, such that the axial compressive motion of the spring is restrained. FIG. 2 shows the proximal end 60 of handle 14 which is coupled to distal end 16 through thin elongated portion 62. Proximal end 60 is suitable for grasping by a surgeon during implantation so that the annuloplasty ring implantation device 12 can be manipulated in the patient during the implantation procedure.

Figure 3:
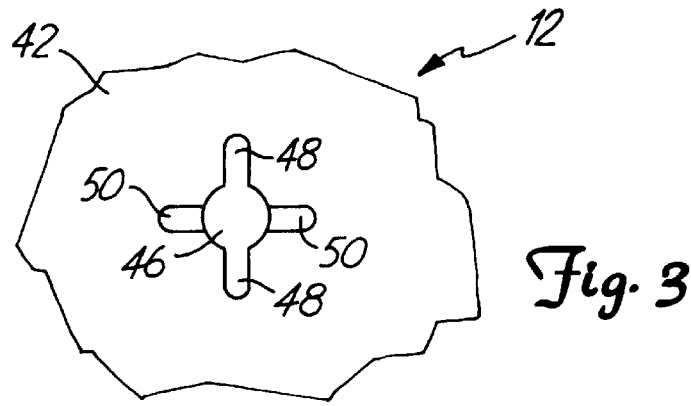
FIG. 3 is a bottom plan view showing the attachment area of the annuloplasty ring implantation device of FIGS. 1 and 2.

FIG. 3 is bottom plan view of a portion of holder 12 showing bottom surface 42. FIG. 3 shows engaging tip opening 46 and key slots 48 which extend all the way through device 12. Also shown in FIG. 3 are key notches 50 which are formed as recesses in the bottom surface 42. Notches 50 do not go all the way through device 12.

Referring to FIGS. 1, 2 and 3, elongated handle 14 is attached to implantation device 12 by aligning engaging tip 24 and locking keys 26 with engaging tip opening 46 and key slots 48, respectively. Engaging tip 24 may then be placed into engaging tip opening 46 and locking keys 26 will pass through key slots 48. Spring distal end 64 of coil spring 32 abuts spring abutting surface 66 of device 12 causing a separation force between handle 14 and device 12 which must be overcome. When locking keys 26 pass all the way through device 12 and emerge from the bottom surface 42, handle 14 is rotated approximately 90° relative to device 12 along the axis of handle 14 and engaging tip opening 46. After the approximate 90° rotation, locking keys 26 will be positioned proximate key notches 50. When the engaging force between handle 14 and device 12 is released, coil spring 32 provides a separation force which causes locking keys 26 to seat in key notches 50. This prevents inadvertent rotation of handle 14 relative to annuloplasty ring implantation device 12 which could lead to undesired separation of the two pieces. This configuration provides a positive lock with device 12, and does not rely on a friction fit.

When the surgeon wishes to separate annuloplasty ring implantation device 12 from handle 14, an engaging force is applied which urges device 12 in a direction toward handle 14. This force frees locking keys 26 from key notches 50 such that handle 14 may be rotated approximately 90° relative to device 12. Following this approximate 90° rotation, locking keys 26 are aligned with key slots 48 such that locking keys 26 and engaging tip 24 may be withdrawn from key slots 48 and engaging tip opening 46, respectively.

Figure 4A:
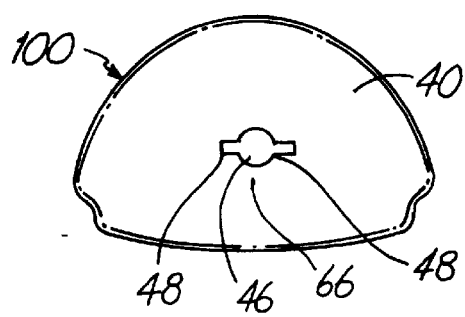
FIG. 4A is a top plan view of an annuloplasty ring sizer template made in accordance with the present invention.
Figure 4B:
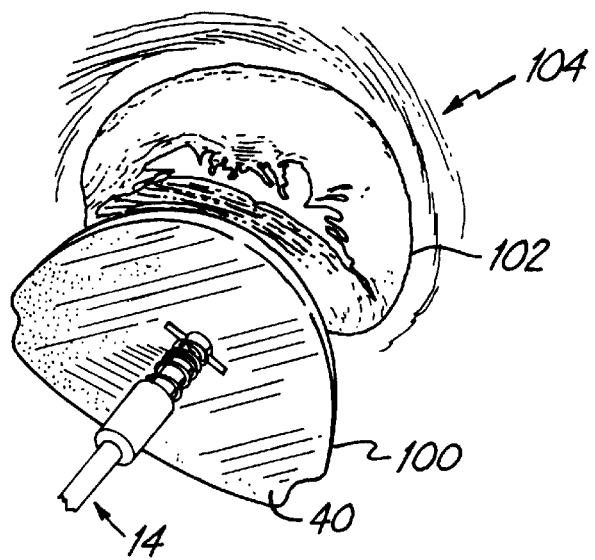
FIG. 4B is a perspective view showing the annuloplasty ring sizer template in accordance with the present invention proximate with a natural heart valve.

FIG. 4A is a top plan view of an embodiment of the present invention in which the annuloplasty ring implantation device is an annuloplasty ring sizer template 100. FIG. 4B is a side perspective view showing annuloplasty ring sizer template 100 used to size the tissue annulus 102 of a natural heart valve 104. As shown in FIGS. 4A and 4B, sizer template 100 includes the top side 40, engaging tip opening 46, key slots 48 and spring abutting surface 66 for receiving elongated handle 14 as discussed above. In operation, the surgeon may selectively remove and attach different size templates 100 to elongated handle 14 until the appropriate size template 100 is found for the specific annulus 102. The spring 32 is compressed as tip 24 is inserted into template 100 and provides a disengaging force against surface 22 and surface 66.

Although shown and described as an annuloplasty sizer template, the present invention can also be utilized as a sizer template for measuring the size of the heart valve tissue annulus which remains after the natural valve is excised before a prosthetic heart valve is implanted. Examples of sizers for use in prosthetic heart valves are shown in U.S. Pat. No. 5,360,014 issued to Sauter et al. and U.S. Pat. No. 5,489,296 issued to Love et al. The shape of the sizer template could be varied to correspond with the generally annular shape of the tissue annulus.

Figure 5A:
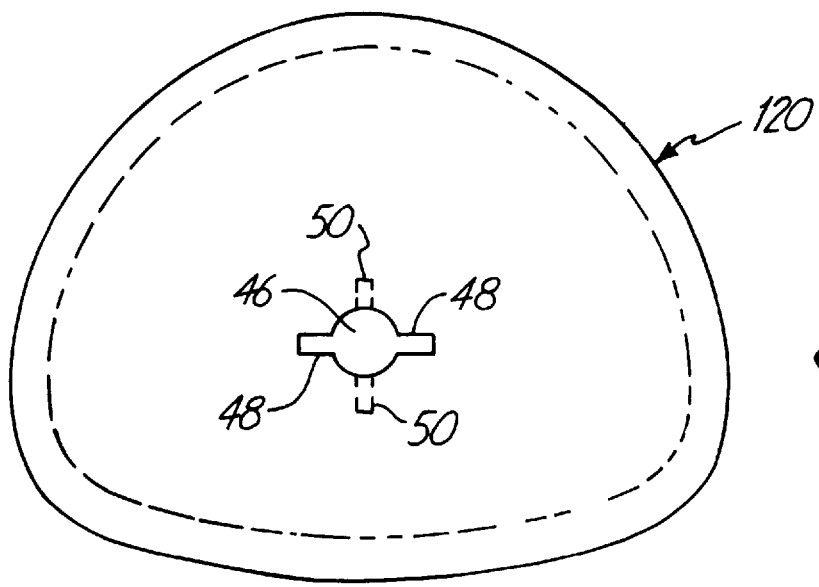
FIG. 5A is a top plan view of an annuloplasty ring holder in accordance with the present invention.
Figure 5B:
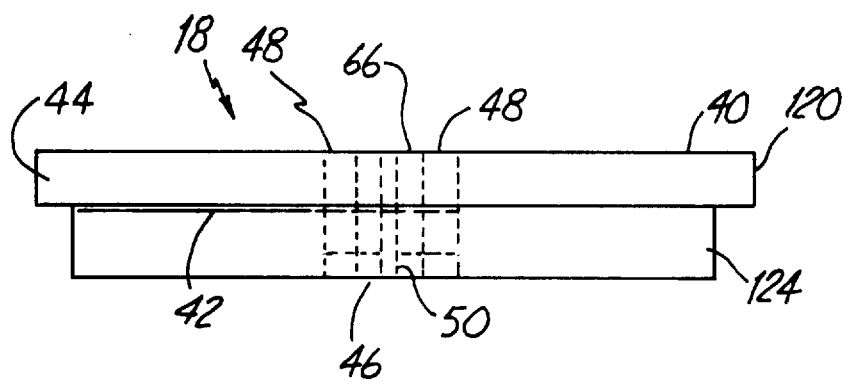
FIG. 5B is a side elevational view of the annuloplasty ring holder of FIG. 5A.
Figure 5C:
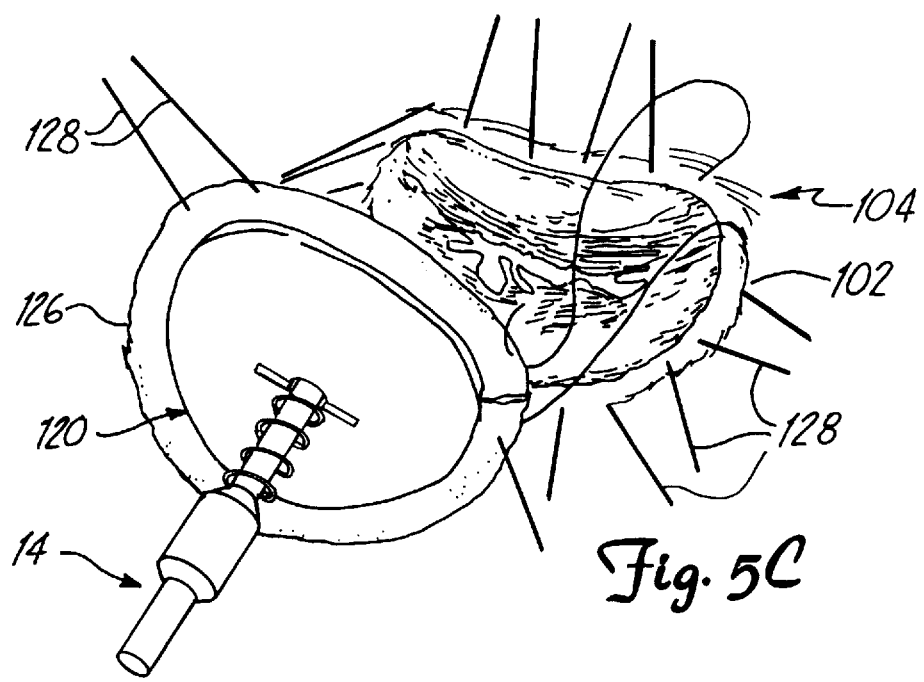
FIG. 5C is a perspective view showing the annuloplasty ring holder of FIG. 5A holding an annuloplasty ring proximate a natural heart valve.

FIGS. 5A, 5B and 5C show an embodiment of the present invention in which the annuloplasty ring implantation device is an annuloplasty ring holder 120. FIG. 5A is a top plan view and FIG. 5B is a side plan view, respectively, of annuloplasty ring holder 120. For consistency, the numbering is the same as that used for the embodiment of FIGS. 1–3. Holder 120 includes engaging tip opening 46 and key slots 48 formed therethrough. Holder 120 includes ring extension 124 for carrying the annuloplasty ring during implantation.

FIG. 5C is a perspective view showing annuloplasty ring holder 120 carrying annuloplasty ring 126 on handle 14 during implantation proximate natural heart valve 104. As shown in FIG. 5C, a plurality of sutures 128 extend through the natural tissue annulus 102 and the annuloplasty ring 126 and are used to attach annuloplasty ring 126 to the natural tissue annulus 102 by techniques known in the art. During implantation, handle 14 can be selectively removed from holder 120 as described above. Removal of handle 14 allows a more unobstructed view of the operation and distal side of device 12 by the surgeon, and facilitates the knotting of sutures 128 to secure the ring to the tissue annulus. The shape of the ring 126 during implantation is maintained since the holder 120 initially remains in place after the handle is removed. After the ring 126 is secured in place in the tissue annulus 102, the handle 14 is reinserted into the holder 120, and the holder 120 is removed.

In preferred embodiments, the sizer templates and holders are made of a substantially clear biocompatible material which can be sterilized, such as polycarbonate or polysulfone. However, the sizer templates or holders may be made of other materials such as metal or a plastic, including Delrin (an acetal). Further, the elongated handle preferably comprises NiTinol (a nickel-titanium alloy) or other shape memory alloys in thin portion 62, a metal or plastic, such as polyphenylsulfone, in proximal end 60, and a metal such as stainless steel in abutting element 20 and tip 24. The coil spring is preferably made of Elgiloy (cobalt alloy) or stainless steel.

The present invention provides a number of advantages. For example, the handle is easily removed from the holder or sizer template during implantation by applying a force directed inward, toward the patient and the holder/sizer, and twisting the handle. Furthermore, the apparatus is easily sterilized and does not include any blind holes which make the sterilization process difficult. The handle and attachment area are easily implemented using existing handles and annuloplasty devices. In addition, if the holder or sizer are made of a clear material, the surgeon can observe the distal side of the device and ensure placement of the ring is correct. Also, the handle can interface with sizers for both valve repair and valve replacement.

The present invention provides numerous advantages over the prior art. The invention provides a positive lock, in both axial and rotational directions. Further, unintentional separation between the pieces during use is prevented. The apparatus is easy and inexpensive to manufacture and retrofit with existing designs. The invention does not require precision machining and the pieces are easily cleaned and sterilized for reuse. The invention provides a low profile implantation device and allows easy viewing by the surgeon during implantation. Further, the low profile provides additional room for suturing and manipulating of the annuloplasty ring by the surgeon. The invention is easy and intuitive to use.

Although the present invention has been described with reference to preferred embodiments, workers skilled in the art will recognize that changes may be made in form and detail without departing from the spirit and scope of the invention. For example, any number of locking keys and key slots, including one or more, may be used with the invention. Further variations on the specific shapes of the engaging tip, locking keys, engaging tip opening and key slots, relative positions and angles described herein are considered within the scope of the present invention. In one embodiment, an internal groove is provided in the tip engaging opening for receiving the locking key such that the locking key does not extend beyond the bottom surface of the annuloplasty ring implantation device. The elongated handle may include a malleable section for positioning the distal end of the holder and/or sizer at different angles during implantation. The low profile of the device is well suited for use with a peel pouch type package. Peel pouch type packages are less costly to manufacture and are more convenient and easier to use than other types of packages for the surgical staff. The low profile holder or sizer templates may be sterilized within the peel pouch type package using steam sterilization technique, or other acceptable methods. The locking pins and key notches may be of any desired shape or relative angle. Further, any appropriate spring or abutting element may be used.

What is claimed is:

1. An apparatus for holding and manipulating an annuloplasty ring during implantation of the annuloplasty ring in a patient, comprising:

an annuloplasty ring implantation device adapted to hold the annuloplasty ring;

an elongated handle having a proximal end for grasping by a surgeon and a distal end;

an engaging tip extending longitudinally from the elongated handle;

a locking key extending generally radially from the engaging tip;

an engaging tip opening formed in the annuloplasty ring implantation device extending into the device from a top surface of the device for receiving the engaging tip therein;

a key slot extending generally radially from the engaging tip opening in the annuloplasty ring implantation device for receiving the locking key therethrough; and a key notch in a bottom surface of the annuloplasty ring implantation device to receive the locking key therein;

wherein the elongated handle is releasably locked to the implantation device by the locking key in the key slot.

2. The apparatus of claim 1 including a coil spring carried on the engaging tip for pressing against the annuloplasty ring implantation device.

3. The apparatus of claim 2 including a locking surface adjacent the distal end of the elongated handle for abutting against the coil spring.

4. The apparatus of claim 1 including:

a second locking key extending generally radially from the engaging tip; and a second key slot extending generally radially from the engaging tip opening for receiving the locking key therethrough.

5. The apparatus of claim 1 wherein the annuloplasty ring implantation device comprises an annuloplasty ring sizer template.

6. The apparatus of claim 1 wherein the annuloplasty ring implantation device comprises an annuloplasty ring holder.

7. The apparatus of claim 1 wherein the annuloplasty ring implantation device is of a clear material.

8. The apparatus of claim 1 wherein the elongated handle is formed from a malleable material.

9. The apparatus of claim 1 wherein the locking key and key slot provide a lock between the elongated handle and the annuloplasty ring implantation device which prevents relative rotational movement therebetween.

10. The apparatus of claim 1 wherein the annuloplasty ring implantation device provides a low profile.

* * * * *